United States Patent [19]
Taniguchi et al.

[11] Patent Number: 4,835,256
[45] Date of Patent: May 30, 1989

[54] HUMAN GAMMA INTERFERON POLYPEPTIDE HAVING GLUTAMINE AS THE NINTH N-TERMINAL AMINO ACID

[75] Inventors: Tadatsugu Taniguchi; Haruo Sugano; Tatsunari Nishi, all of Tokyo, Japan; Jan T. Vilcek, New York; Yum K. Yip, Forest Hills, both of N.Y.

[73] Assignees: New York University & Juridical Foundation, New York, N.Y.; Japanese Foundation for Cancer Research, Tokyo, Japan

[21] Appl. No.: 129,924

[22] Filed: Dec. 3, 1987

Related U.S. Application Data

[63] Continuation of Ser. No. 786,142, Oct. 8, 1985, abandoned, and a continuation-in-part of Ser. No. 765,179, Aug. 13, 1985, abandoned, which is a continuation of Ser. No. 516,264, Jul. 22, 1983, abandoned, which is a continuation of Ser. No. 325,126, Nov. 27, 1981, abandoned, said Ser. No. 786,142, is a continuation of Ser. No. 697,422, Feb. 1, 1985, abandoned, which is a continuation of Ser. No. 447,794, Dec. 8, 1982, abandoned, which is a continuation-in-part of Ser. No. 428,953, Sep. 30, 1982, abandoned.

[51] Int. Cl.$^4$ .................. C07K 13/00; C07K 15/26; A61K 45/02; C12P 21/00
[52] U.S. Cl. .................................. 530/351; 435/68; 435/811; 424/85.5
[58] Field of Search ............. 530/351; 424/85.5; 435/68, 811

[56] References Cited

PUBLICATIONS

Gray et al., Nature, vol. 295, pp. 503–508, 1982.
Rubins et al., Proc. Natl. Acad. Sci., vol. 77, pp. 5928–5932, 1980.
Lep et al., Proc. Natl. Acad. Sci., vol. 78, pp. 1601, 1605, 1981.
Taniguchi et al., Proc. Natl. Acad. Sci., vol. 78, pp. 3469–3472, 1981.
Chemical Abstracts, vol. 97, Abstract No. 18357v, 1982.
Chemical Abstracts, vol. 93, Abstract No. 130300d, 1980.

*Primary Examiner*—Blondel Hazel
*Attorney, Agent, or Firm*—Fitzpatrick, Cella, Harper & Scinto

[57] ABSTRACT

Disclosed is a novel DNA which shows complementarity to human interferon-γ mRNA, a recombinant plasmid containing the DNA, a microorganism containing the recombinant plasmid and a method of producing the same as well as a process for producing a polypeptide having human interferonγ activity using the microorganism.

1 Claim, 3 Drawing Sheets

```
CACATTGTCTGATCATCTGAAGATCAGCTATTAGAAGAGAAAGATCAGTTAAGTCCTTTGGACCTGATCAGCTTGATACAAGAACTACTGATTT met lys tyr thr ser tyr ile leu ala phe gln leu cys ile val leu
CAACTTCTTTGGCTTAATTCTCTCGGAAACG ATG AAA TAT ACA AGT TAT ATC TTG GCT TTT CAG CTC TGC ATC GTT TTG gly ser leu gly CYS TYR CYS GLN ASP PRO TYR VAL GLN LEU ASN GLU LYS LYS TYR PHE ASN ALA
GGT TCT CTT GGC TGT TAC TGC CAG GAC CCA TAT GTA CAA GAA AAC CTT AAG AAA TAT TTT AAT GCA GLY HIS SER ASP VAL ALA ASP ASN GLY THR LEU PHE ILE LEU LYS ASN TRP LYS GLU GLU SER ASP
GGT CAT TCA GAT GTA GCG GAT AAT GGA ACT CTT TTC TTA GGC ATT TTG AAG AAT TGG AAA GAG GAG AGT GAC ARG LYS ILE MET GLN SER GLN ILE VAL SER PHE TYR PHE LYS LEU ASN PHE LYS ASP ASP GLN SER
AGA AAA ATA ATG CAG AGC CAA ATT GTC TCC TTT TAC TTC AAA CTT TTT AAA GAT GAC CAG AGC ILE GLN LYS SER VAL GLU THR ILE LYS ASP MET ASN VAL LYS PHE PHE ASN SER ASN LYS LYS ARG
ATC CAA AAG AGT GTG GAG ACC ATC AAG GAC ATG AAT GTC AAG TTT TTC AAT AGC AAC AAA AAG CGA ASP ASP PHE GLU LYS LEU THR ASN TYR SER VAL THR SER LEU ASN VAL GLN ARG LYS ALA ILE HIS GLU LEU
GAT GAC TTC GAA AAG CTG ACT AAT TAT TCG GTA ACT GAC TTG AAT GTC CAA CGC ATA CAT GAA CTC ILE GLN VAL MET ALA GLU LEU SER PRO ALA ALA LYS THR GLY LYS ARG LYS SER GLN MET LEU PHE ARG
ATC CAA GTG ATG GCT GAA CTG TCG CCA GCA GCT AAA ACA GGG AAG CGA AAA AGG AGT CAG ATG CTG TTT CGA GLY ARG ARG ALA SER GLN
GGT CGA AGA GCA TCC CAG TAA TGGTTGTCCTGCCTGCAATATTTGAATTTAAATCTAATTATTAATATTAACATTATTAACATTATTA TATGGGAATATATTTTAGACTCATCATCAATCAAATAAGTATTTATAATAGCAACTTTTGTGTAATGAAAATGAATATCTATTAATAATATGTATTA TTTATAATTCCTATATCCTGTGACTGTCTCACTTAATCCTTGTTTTTCTGACTAATTAGGCAAGGCTATGTGATTACAAGGCTTTATCTCAGGGG CCAACTAGGCAGCCAACCTAAGCAAGATCCCATGGGTTGTGTGTTTATTTCACTTGATGATACAATGAACACTTATAAGTGAAGTGATACTATCC

AGTTACTA CCCCCCC·····
```

Nucleotide sequence and deduced amino acid sequence of plasmid pIFNγ-G4 insert

HUMAN GAMMA INTERFERON POLYPEPTIDE HAVING GLUTAMINE AS THE NINTH N-TERMINAL AMINO ACID

CROSS-REFERENCE TO RELATED APPLICATIONS

This application is a continuation of application Ser. No. 786,142 filed Oct. 8, 1985 (now abandoned), which is a continuation of application Ser. No. 697,422, filed Feb. 1, 1985 (now abandoned), which is a continuation of application Ser. No. 447,794, filed Dec. 8, 1982 (now abandoned), which is a continuation-in-part of application Ser. No. 428,953, filed Sept. 30, 1982 (now abandoned). This application is also a continuation-in-part of application Ser. No. 765,179, filed Aug. 13, 1985 (now abandoned), which is a continuation of application Ser. No. 516,264, filed July 22, 1983 (now abandoned), which is a continuation of application Ser. No. 325,126, filed Nov. 27, 1981 (now abandoned).

BACKGROUND OF THE INVENTION

The present invention relates to a DNA which, with distinct nucleotide sequence, shows complementarity to human interferon-γ (referred to as IFN-γ hereinafter) messenger RNA (referred to as mRNA hereinafter) and a recombinant plasmid containing the DNA. The DNA also codes for biologically active IFN-γ. The present invention also pertains to a microorganism containing the recombinant plasmid.

Interferons (referred to as INFs hereinafter) are proteins (some of which are in glycosylated form) with antiviral activity, discovered originally by Isaacs and Lindenmann in 1957. It is known that at least three types of IFN, namely IFN-α, IFN-β, IFN-γ, are produced. Subsequent studies have indicated antitumor activity of the substances in addition to antiviral activity and hence a wide clinical application of these substances is expected. For instance, it has been reported that IFN may be effective against various viral diseases and malignant tumors.

However, because of its species-specificity, only the IFN of human origin can be applied to human beings. The use of the IFN has been quite limited because of difficulties in mass production. Only recently, recombinant DNA technology has been applied to the production of human IFN-α and IFN-β by microorganisms such as *Escherichia coli* and *Saccharomyces cerevisiae*. For the same reasons, development of technology to produce human IFN-γ is also in demand.

To this end, a novel DNA and recombinant plasmid have been developed for producing human IFN-γ with ease and in large quantities.

It has been reported that IFN-γ may have more potent antitumor activity compared to other IFNs [Proc. Natl. Acad. Sci., USA, 77, 5928–5932 (1980)]. Recently, cloning and expression of an IFN-γ cDNA in *Escherichia coli* as well as the nucleotide sequence of the cDNA have been reported by Gray et al., Nature, 295, 503 (1982).

However, possibility for the presence of IFN-γ cDNA sequence which differs from the sequence reported by Gray et al., could not be ruled out. If present, the IFN protein coded for by such cDNA could manifest different biological activities and may be of great use for clinical application.

SUMMARY OF THE INVENTION

In accordance with the present invention, a DNA which shows complementarity to human IFN-γ mRNA is prepared using human IFN-γ mRNA as a template and a novel recombinant plasmid containing the DNA is prepared. In addition, the recombinant plasmid may be inserted into a host microorganism. The DNA and the recombinant plasmid may be used, inter alia, for amplification of human IFN-γ gene in bacteria such as *Escherichia coli*. Such bacteria will be useful for the production of human IFN-γ in large quantities at low cost.

The DNA and the recombinant plasmid of the present invention are prepared by the following general procedure.

First, cytoplasmic RNA is extracted from human mononuclear cells induced by a T cell mitogen such as phytohemagglutinin, concanavalin A (Con A) in the presence of a phorbol ester such as 12-O-tetradecanoylphorbol 13-acetate, mezerein or related compounds thereof. Alternatively, the RNA can be isolated from human T-cells or human T-cell lines of the thymus, lymphoblasts and peripheral blood cells induced by other inducers such as Staphylococcal enterotoxin A (SEA) or B (SEB) or deacetylthymosin α.

From this RNA, the human IFN-γ mRNA having poly A (polyadenylic acid) is isolated. A double stranded DNA is synthesized, for example, by reverse transcriptase, with the mRNA preparation having high IFN-γ mRNA activity, as a template. A recombinant is obtained by inserting the synthesized DNA into a vector DNA such as *Escherichia coli* plasmid DNA by the technique of in vitro DNA recombination. Recombinant plasmids having the inserted DNA which shows complementarity to the human IFN-γ mRNA are selected.

DETAILED DESCRIPTION OF THE INVENTION

Human mononuclear cells are isolated from lymphocytes-rich "platelet residues" by centrifugation at 400×g for 30 minutes on a Ficoll/Hypaque gradient. The cells are treated with 5 ng/ml of a phorbol ester such as 12-O-tetradecanoylphorbol 13-acetate for 2 hrs. Then a T-cell mitogen such as PHA (5 μg/ml) or Con A or the like is added and the mixture is kept at 37° C. for 20 to 40 hours. Cells are collected and disrupted, and the nuclei are removed. Entire cytoplasmic RNAs are extracted with, for example, phenol.

Alternatively cells are disrupted, and both DNAs and RNAs are extracted with, for example, phenol. The DNAs are decomposed with DNAase and removed followed by extracting the RNAs.

The thus extracted RNAs are dissolved in a salt solution of NaCl or KCl at a high concentration such as 0.5M and put on a column of oligo (dT) cellulose to adsorb mRNA having poly(A) on the column. Elution is carried out with water, a salt solution at a low concentration such as 10 mM Tris-HCl buffer, or the like to isolate mRNA having poly(A).

The isolated mRNA is fractionated by sucrose density gradient centrifugation. IFN mRNA activity in each fraction is checked by determining interferon activity (antiviral activity) of the protein which is synthesized in oocytes of African claw toad (*Xenopus laevis*) after microinjecting a part of the mRNA in each fraction. The determination of IFN activity is carried out according to the method described in Japan J. Microbiol. 18, 449-456, (1974).

Then, a DNA showing complementarity to the mRNA is synthesized in vitro by a reverse transcriptase, which is obtained from avian myeloblastosis virus (AMV), using, as the template, an mRNA having the highest interferon mRNA activity.

The synthesis is carried out as follows.

An mRNA is reacted at an appropriate temperature (e.g. 41° C.) for an appropriate period (e.g. 90 min.) with oligo (dT), MgCl$_2$ (e.g. 5 mM), NaCl (e.g. 30 mM), mercaptoethanol (e.g. 5 mM) and Tris-HCl buffer (e.g. pH 8.0, 40 mM) using a reverse transcriptase together with deoxyadenosine triphosphate (dATP), deoxythymidine triphosphate (dTTP), deoxyguanosine triphosphate (dGTP) and deoxycytidine triphosphate (dCTP) (e.g. 0.5 mM) as substrate.

The thus obtained reaction product is subjected to deproteinization with, for example, phenol, and the template RNA is removed by alkali or ribonuclease treatment.

Double stranded cDNA is synthesized by reverse transcriptase in a similar way as the synthesis of the first strand (i.e. single stranded cDNA) as described above except that mRNA and oligo (dT) are not present. By using *Escherichia coli* DNA polymerase I instead of reverse transcriptase, the double stranded cDNA can also be synthesized. The cDNA which is synthesized by the above described procedure is treaded with nuclease S$_1$ which can be obtained from *Aspergillus oryzae* in the presence of ZnCl$_2$ (e.g. 1 mM), sodium acetate buffer (e.g. 0.1M, pH 4.5), NaCl (e.g. 0.2M), etc.

Alternatively, double stranded cDNA can be synthesized as described by Land et al., [Nucleic Acids Res. 9, p. 2251-2266 (1981)]; The single stranded cDNA is treated by terminal transferase with dCTP as substrate to add deoxycytidyl residues at the 3' end of the cDNA. After deproteinization, the elongated cDNA is incubated with oligo(dG)$_{12-18}$, reverse transcriptase, dATP, dGTP, dCTP and dTTP to synthesize the second strand. Reverse transcriptase can be replaced by DNA polymerase I in this reaction.

On this DNA, deoxycytidyl residues are elongated at both 3' ends of the synthesized DNA by incubating with a terminal transferase purified from calf thymus in the presence of potassium cacodylate buffer (e.g. pH 7.6, 0.14M), Tris (base) (e.g. 0.03M), dithiothreitol (e.g. 0.1 mM), CoCl$_2$ (e.g. 1 mM) and dCTP (e.g. 1 mM) at an appropriate temperature (e.g. 37° C.) for an appropriate period (e.g. 20 min.).

On the other hand, a plasmid DNA which is used as a vector DNA, e.g. *Escherichia coli* plasmid pBR322DNA [Gene vol. 2, p. 95-113 (1977)] or derivatives thereof is used. The double stranded DNA is inserted into a restriction site of the plasmid. For example, p321, obtained from P. Berg, Stanford University which is a derivative of pBR322 [Okayama & Berg; Molecular and Cellular Biology, vol. 2, p. 161-170 (1982)] is treated with KpnI [*Klebsiella pneumoniae*, Takara Shuzo Co.] in a suitable solution, for example Tris-HCl buffer (e.g. pH 7.5, 6 mM), MgCl$_2$ (e.g. 6 mM), NaCl (e.g. 6 mM), 2-mercaptoethanol (e.g. 6 mM) and 0.02% bovine serum albumin to cut a KpnI site in p321. Thereafter deoxyguanyl residues are elongted at both 3' ends in the same way as for the above-described synthesized double stranded DNA by using dCTP instead of dCTP as substrate for the terminal transferase.

Synthetic double stranded DNA and plasmid DNA which are chain-elongated at both 3' ends as described above are incubated at an appropriate temperature for an appropriate period with Tris-HCl buffer (e.g. pH 7.5, 50 mM), NaCl (e.g. 0.1M), EDTA (e.g. 5 mM), or the like to form hybrid plasmids [Taniguchi et al, Nature vol. 274, p. 223-228 (1978)]. Then, a transformable *Escherichia coli* strain, e.g. *Escherichia coli* χ1776 (Molecular Cloning of Recombinant DNA, Scott, W. A. & Werner, R. editors, Academic Press p. 99-114, 1977) is transformed by the hybrid plasmids by the method of Enea et al. (J. Mol. Biol., vol. 96, p. 495-509, 1975) or the like.

In the novel recombinant plasmid DNA thus obtained, there exists a vector DNA gene, e.g. β-lactamase (enzyme that destroys ampicillin) gene derived from *Escherichia coli* plasmid pBR322. Therefore, the transformed *Escherichia coli* shows resistance to ampicillin. The following technique is generally used to pick up a strain with a novel recombinant plasmid DNA having a gene which shows complementarity to the human IFN mRNA among these ampicillin resistant (Ap$^R$) strains.

First, [$^{32}$P] labelled DNA is synthesized with the RNA having IFN mRNA activity described above as a template and the DNA is hybridized with mRNA extracted, without induction by PHA (therefore, IFN mRNA synthesis is not induced), from the human mononuclear cells by incubating at a high temperature (e.g. 65° C.) in a reaction mixture containing, for example NaCl (e.g. 0.5M). Then, the hybridized DNA (Probe A) and non-hybridized DNA (Probe B) are separated by hydroxyapatite column chromatography. Next, filter-fixed DNAs of transformants are hybridized separately with Probe B or Probe A according to the technique of Grunstein-Hogness (Proc. Nat. Acad. Sci. USA. vol. 72, p. 3961-3965, 1975) and strains having a DNA hybridizable with Probe B but not or barely with Probe A are discerned by autoradiography.

Then, plasmid DNA is isolated from each of the discriminated strains and hybridized with mRNA having IFN mRNA activity by incubating at a high temperature (e.g. 53° C.) in the presence of 80% (w/v) formamide, 0.4M NaCl, etc. Since the mRNA hybridized with cDNA portion of the plasmid DNA from the above-described strain can be retained on a nitrocellulose filter, whereas unhybridized mRNA can not under certain conditions (refer to Example below and Nygaard, A. P. & Hall, B. D., Biochem. Biophys. Res. Commun. Vol. 12, p. 98-104, 1963), this mRNA can be recovered selectively from the filter at a high temperature (e.g. 60° C.) in a solution such as 90% (v/v) formamide and thereafter injected into oocytes of *Xenopus laevis*.

When interferon is synthesized in the oocytes, the DNA used for hybridization must contain a DNA which is complementary to interferon mRNA; and by this method, a recombinant plasmid DNA having a gene showing complementarity to the human IFN-γ mRNA can be isolated.

Alternatively, a part of the known DNA sequence of IFN-γ is synthesized and used as a probe for the screening. The probe DNA is synthesized by a conventional triester method [JACS, 97, 7327 (1975)] and the screening is carried out by in situ hybridization essentially as described above.

The cloned cDNA can be readily expressed in, for example, cultured monkey cells such as COS-7 cells. (Gulzman, Cell, 23, 175, (1981).

The novel recombinant plasmids of the present invention are used for the mass production of IFN-γ by a microorganism such as *Escherichia coli* or eukaryotic cells.

One specific embodiment of the present invention is illustrated by the following representative example.

EXAMPLE (1) Induction of IFN-γ in human lymphocytes:

Human mononuclear cells are isolated from lymphocytes-rich platelet residues [Proc. Natl. Acad. Sco., U.S.A. 78 (6), 3469–3472 (1981)] by Ficoll/Hypaque density gradient centrifugation at 400×g. $6 \times 10^6$/ml mononuclear cells are treated with 5 ng/ml 12-O-tetradecanoylphorbol 13-acetate (TPA) obtained from Consolidated Midland in RPMI 1640 medium without serum (Product of GIBCO) for 2 hours. Then, 5 μg/ml purified phytohemagglutinin (PHA) is added. After keeping at 37° C. for 20 to 40 hours, the cells are recovered with a rubber policeman into a physiological saline solution buffered with sodium phosphate. About $4 \times 10^9$ cells are pelleted under centrifugation at 800×g for 5 minutes and resuspended in a physiological saline solution buffered with sodium phosphate. Then, the suspension is dispersed into 80 ml of a mixture of 10 mM ice-cooled Tris-HCl (pH 7.5) containing 10 mM of ribonucleotide-vanadyl complex [S. L. Berger and C. S. Birkenmeier, Biochemistry 18, 5143–5149 (1979)], 10 mM NaCl and 1.5 mM $MgCl_2$ in 150 ml-Corex tube. Nonidet P-40 (distributed by SIGMA, USA) is added to a final concentration of 0.3% (v/v) and the mixture is centrifuged in a Sorvall GS rotor at 300 rpm for 5 minutes to remove nuclei. The supernatant is put into a Corex tube containing 4 ml of 10% sodium dodecylsulfate, 4 ml of 2M Tris-HCl (pH 9.0) and 2 ml of 0.25M EDTA and immediately subjected to extraction with phenol. The extraction is repeated two times and RNA is deposited with ethanol. 250 mg of the thus obtained RNA is dissolved in 10 ml of 1 mM EDTA. After incubation at 65° C. for 2 minutes, 2.5 ml of a salt solution at a high concentration [0.5M Tris-HCl (pH 7.5), 1M NaCl, 50 mM EDTA] is added to the solution. The mixture is subjected to oligo dT cellulose column (P-L Biochemicals) chromatography. Adsorbed mRNAs having poly A are eluted by a salt solution at a low concentration [10 mM Tris-HCl, (pH 7.5)] or by water to obtain 250 μg mRNA having poly A.

(2) Fractionation of mRNA by sucrose density gradient centrifugation:

The mRNA is deposited with ethanol and dissolved in 0.5 ml of 1 mM EDTA. After heating a 70° C. for 2 minutes, the solution is centrifuged at 26,000 rpm and 4° C. for 19 hours in the Hitachi PRS 40 Ti Rotor in 5 to 25% sucrose density gradient prepared in a solution of 50 mM Tris-HCl, 0.2M NaCl and 1 mM EDTA. Ribosomal RNA is centrifuged with another tube for the use of size marker. The former is recovered in 15 fractions and IFN-γ mRNA activity is measured in a part of the fractions. The results are illustrated in Table 1. Most IFN-γ mRNA activity is present in fraction No. 8.

TABLE 1

Partial purification of human IFN-γ in RNA by sucrose gradient centrifugation

| Fraction No. | IFN activity from *Xenopus laevis* oocytes into which mRNA from each fraction was injected (units/ml) |
|---|---|
| 1 | N.D. |
| 2 | N.D. |
| 3 | N.D. |
| 4 | N.D. |
| 5 | N.D. |
| 6 | <10 |
| 7 | 250 |
| 8 | 1250 |
| 9 | 80 |
| 10 | <10 |
| 11 | <10 |
| 12 | <10 |
| 13 | N.D. |
| 14 | N.D. |
| 15 | N.D. |

N.D. not determined (3) Preparation of cDNA and dsDNA

In this step, 14.4 μg of mRNA in fraction No. 8 is incubated at 37° C. for 1 hour in a reaction solution containing 0.5 mM each of dATP, dGTP, dTTP and dCTP, 1 μg of oligo(dT), 8 units of AMV transcriptase (product of Bethesda Research Lab.), 5 mM $MgCl_2$, 30 mM NaCl, 5 mM mercaptoethanol and 40 mM Tris-HCl (pH 8.0). cDNA complementary to the mRNA is formed in the solution. Protein is removed with phenol and RNA is removed by treating at 37° C. for 15 hours with 0.3N NaOH.

Then, the cDNA is treated at 37° C. for 20 minutes with 2 units of terminal transferase (product of Bethesda Research Lab.) in 30 μl of reaction solution (2.65 μg of DNA, 0.14M potassium cacodylate, 30 mM Tris, 1 mM dCTP, 0.1 mM dithiothreitol, 1 mM $CoCl_2$, pH 7.6) to add about 23 deoxycytidyl residues to the end of the cDNA. 3 μl of 0.5M EDTA (pH 8.0) is added to stop the reaction and protein is removed with phenol. Water layers are collected and DNAs are recovered by the addition of ethanol. 2.32 μg of the thus recovered DNA is treated at 37° C. for 1 hour with the reverse transcriptase reaction solution mentioned above except that the oligo(dT) is replaced with 1 μg of oligo $(dG)_{12-18}$ (Collaborative Research Inc.) to obtain 4.24 μg of double stranded DNA (dsDNA).

Then, 1.78 μg of the dsDNA is treated at 37° C. for 20 minutes with 1 unit of terminal transferase in 20 μl of reaction solution [1.78 μg of dsDNA, 0.14M potassium cacodylate (pH 7.6), 0.03M Tris-HCl, 0.1 mM dithiothreitol, 1 mM $CoCl_2$, 1 mM dCTP] to add about 31 deoxycytidyl residues to both 3' ends of the dsDNA.

(4) Cloning of dsDNA:

In this step, 15.6 μg of plasmid p321 is treated at 37° C. for 1 hour with Kpn (*Klebsiella pneumoniae* OK8, product of Takara Shuzo Co.) in 100 μl of reaction solution [6 mM Tris-HCl (pH 7.5), 6 mM $MgCl_2$, 6 mM NaCl, 6 mM 2-mercaptoethanol, 0.02% bovine serum albumin] to cut a Kpn site in plasmid p321. The cut plasmid p321 is treated at 37° C. for 20 minutes with 2 units of terminal transferase (product of Bethesda Research Lab.) in 100 μl of reaction solution [15.6 μg of DNA, 0.14M potassium cacodylate, 30 mM Tris-HCl (pH 7.6), 1 mM dGTP, 0.1 mM dithiothreitol, 1 mM CoCl2] to add about 35 deoxyguanines to both 3' ends of p321 DNA.

Then, 80 ng of the thus obtained plasmid DNA and 30 ng of the dsDNA obtained in step (3) are incubated at 65° C. for 2 minutes, at 46° C. for 120 minutes, at 37° C. for 60 minutes and at room temperature for 60 minutes in a solution consisting of 20 mM Tris-HCl (pH 7.5), 100 mM NaCl and 1 mM EDTA to hybridize both DNAs. *Escherichia coli* χ1776 (ATCC 31244) is transformed with the hydrid DNA by the method of Enea et al. [J. Mol. Biol., 96, 495–509 (1975)]. About 5,500 of ampicillin resistant (ApR) strains are isolated. 3,200 strains thereof are chosen and the DNA of each strain is fixed on nitrocellulose filters in duplicate. Then, 6 strains which hybridize at 37° C. strongly to a probe oligodeoxynucleotides labelled with $^{32}PO_4^{--}$, $^{32}P$-TGCCAGGACCCATA, are selected [Grunstein-Hogness method, Proc. Natl. Acad. Sci. U.S.A., 72, 3961 (1975)].

The thus obtained 6 strains are subjected to the same screening method as above at 44° C. to obtain strongly hybridized plasmid which is named pIFNγ-G4.

Figure 1:
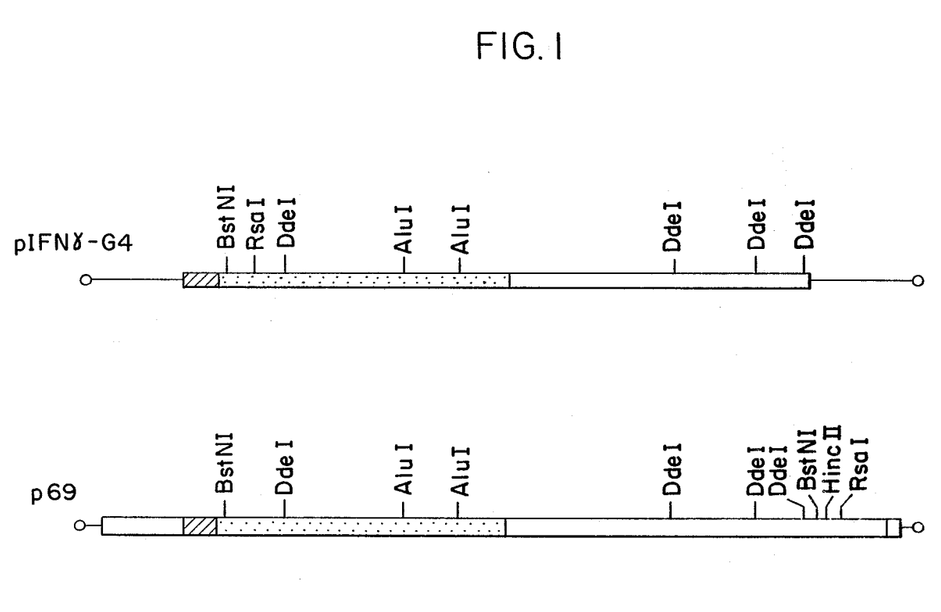
FIG. 1 is a restriction endonuclease cleavage map of pIFNγ-G4 cDNA. cDNA of P69 reported by Gray et al. is also illustrated for comparison.

(5) Nucleotide sequence of the plasmid, pIFNγ-G4:

The cDNA insert of the plasmid pIFNγ-G4 obtained above is digested by various restriction endonucleases and its cleavage map is illustrated in FIG. 1. The restriction enzyme cleavage map of the cDNA from plasmid P69 reported by Gray et al. [Nature, 295, 503 (1982)] is also presented in FIG. 1 for comparison. One notable difference in these two cDNA clones is the presence of an additional Rsa I [product of New England Biolabs. U.S.A.] site in the clone pIFNγ-G4 which is not present in the cDNA clone P69 reported by Gray et al.

Figure 2:
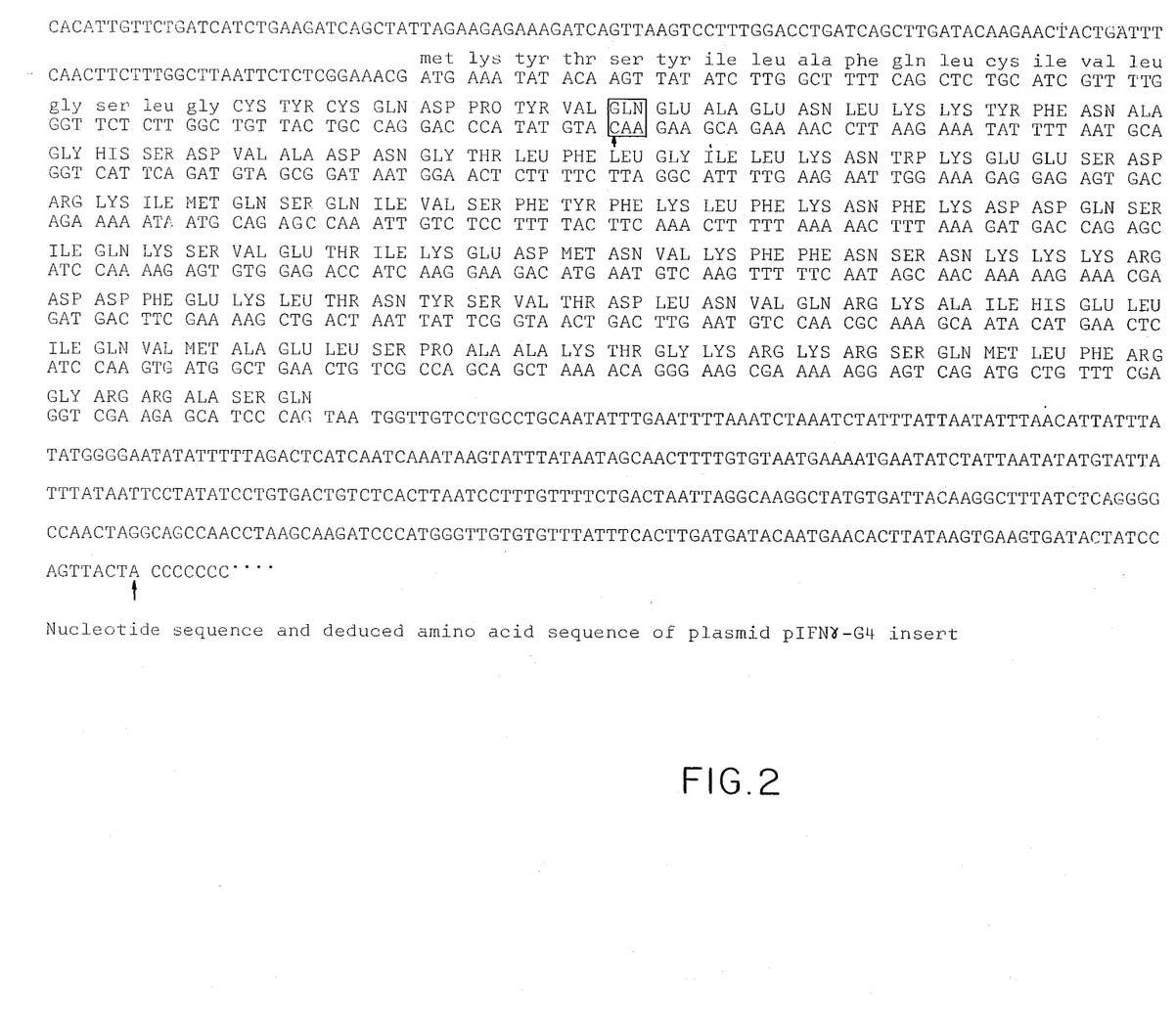
FIG. 2 represents the complete nucleotide sequence of the cDNA from pIFNγ-G4.

Next, the complete nucleotide sequence of the DNA which is likely to have the nucleotide sequence divergence is determined according to the Maxam-Gilbert method (Proc. Natl. Acad. Sci., U.S.A. 74, 560–564 (1977)). The sequence is set forth in FIG. 2. Part of the sequence which corresponds to the reported N-terminal region of the human IFN-γ (Gray et al., Nature, 295, 503 (1982)) is presented below.

A cDNA clone for the human IFN-γ reported in Nature 295, 503 (1982) has the following nucleotide sequence which corresponds to the above sequence of pIFNγ-G4.

Thus, the cDNA sequence of the plasmid pIFNγ-G4 differs from the reported IFN-γcDNA by two nucleotides (indicated by arrows in FIG. 2) resulting in one amino acid replacement (Lys→Gln) of the IFN-γ polypeptide. The replaced amino acid is boxed in FIG. 2.

Figure 3:
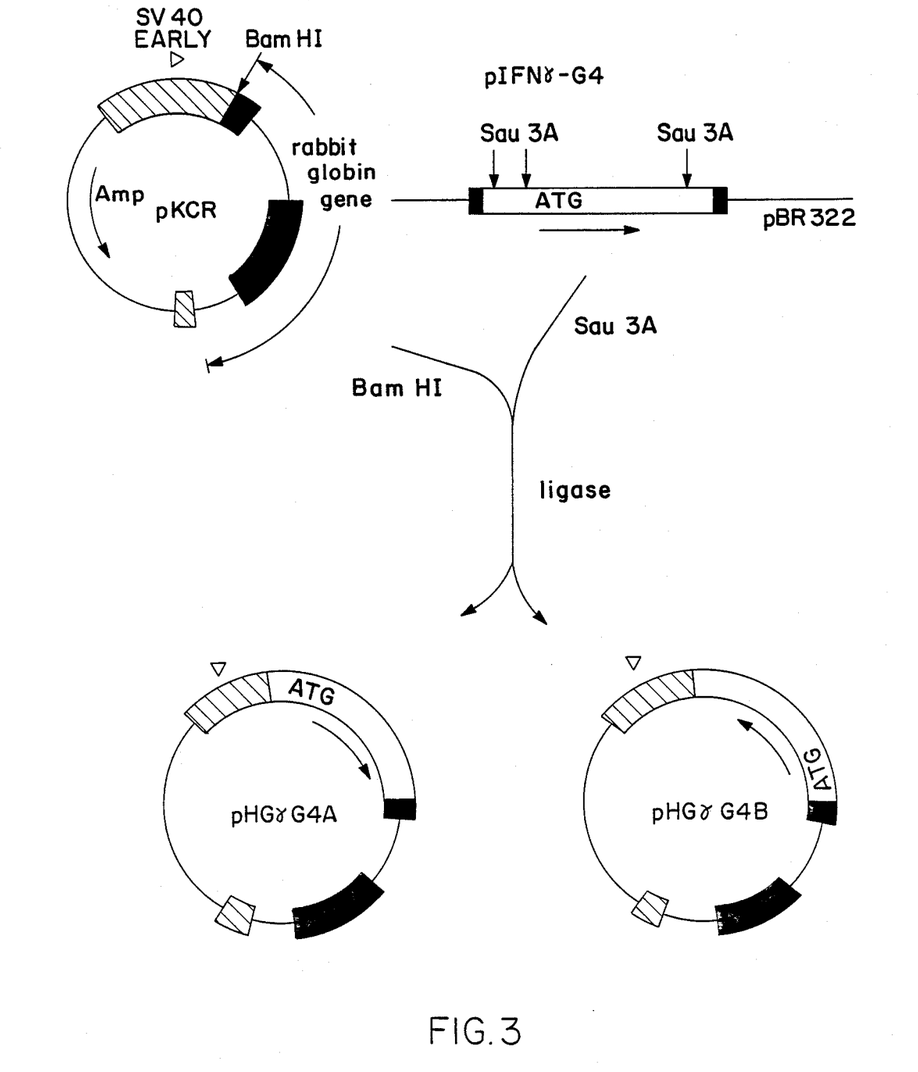
FIG. 3 illustrates the construction of the plasmid pHGγG4 which is used for the expression of the cDNA in monkey cells.

In order to establish that the novel cDNA codes for biologically active human IFN-γ, the cDNA was cleaved with Sau3A. (product of Takara Shuzo Co., Ltd.) and the DNA which encompasses the entire coding region of the IFN-γmRNA was introduced into a plasmid pKCR (O'Hare et al.. Proc. Natl. Acad. Sci., U.S.A., 78, 1527 (1981)) as illustrated in FIG. 3. The cDNA is linked downstream from the SV-40 early promoter to construct plasmid pHGγG4A.

The plasmid DNA, pHGγG4A, was transferred into COS-7 cells by the procedure of McCutchan and Pagano, J. Natl., Cancer Inst., 41, 351 (1968). Seventy two hours after transfection, interferon activity in the culture medium was determined and the results are set forth in Table 2 below. As shown in Table 2, activity characteristic of human IFN-γ was produced in the medium which demonstrates that the cDNA in the novel recombinant plasmid, pIFNγ-G4, codes for human IFN-γ.

TABLE 2

| Sample | Anti huγIFN serum | IFN activity (units/ml) |
|---|---|---|
| native huγIFN | − | 256 |
| " | + | <4 |
| COS-7 cell culture fluid after transfection by pHGγG4 | − | 32 |
| COS-7 cell culture fluid after transfection by pHGγG4 | + | <4 |

Plasmid, pIFNγ-G4, has been deposited with the American Type Culture Collection, Rockville, Md., U.S.A. under accession number *Escherichia coli* IG-G4

ATCC 39123.

What is claimed is:

1. Interferon-γ polypeptide, comprising the amino acid sequence illustrated in FIG. 2.

* * * * *

UNITED STATES PATENT AND TRADEMARK OFFICE
CERTIFICATE OF CORRECTION

PATENT NO. : 4,835,256
DATED : May 30, 1989
INVENTOR(S) : TADATSUGU TANIGUCHI, ET AL.   Page 1 of 2

It is certified that error appears in the above-identified patent and that said Letters Patent is hereby corrected as shown below:

IN [56] REFERENCES CITED

PUBLICATIONS, "Lep et al.," should read --Yip et al.,--.

PUBLICATIONS, "Chemical Abstracts, vol. 97, Abstract No. 18357v, 1982." should read --Chemical Abstracts, vol. 97, Abstract No. 18357j, 1982.--.

IN [57] ABSTRACT

Line 6, "interferon$\gamma$" should read --interferon-$\gamma$--.

COLUMN 3

Line 39, "treaded" should read --treated--.

COLUMN 4

Line 8, "dCTP instead of dCTP" should read --dGTP instead of dCTP--.

UNITED STATES PATENT AND TRADEMARK OFFICE
CERTIFICATE OF CORRECTION

PATENT NO. : 4,835,256
DATED : May 30, 1989
INVENTOR(S) : TADATSUGU TANIGUCHI, ET AL.  Page 2 of 2

It is certified that error appears in the above-identified patent and that said Letters Patent is hereby corrected as shown below:

COLUMN 5

Line 20, "Sco.," should read --Sci.,--.

COLUMN 8

Line 23, "transferred" should read --transfected--.

Signed and Sealed this

Twenty-seventh Day of February, 1990

Attest:

JEFFREY M. SAMUELS

Attesting Officer  Acting Commissioner of Patents and Trademarks

UNITED STATES PATENT AND TRADEMARK OFFICE
CERTIFICATE OF CORRECTION

PATENT NO. : 4,835,256

DATED : May 30, 1989

INVENTOR(S) : TADATSUGU TANIGUCHI, ET AL.

It is certified that error appears in the above-identified patent and that said Letters Patent is hereby corrected as shown below:

ON THE TITLE PAGE,
IN [73] ASSIGNEES

"New York University & Juridical Foundation, New York, N.Y.; Japanese Foundation for Cancer Research, Tokyo, Japan" should read --New York University, New York, N.Y.; Juridical Foundation, Japanese Foundation for Cancer Research, Tokyo, Japan--.

Signed and Sealed this

Fourteenth Day of July, 1992

Attest:

DOUGLAS B. COMER

*Attesting Officer*   *Acting Commissioner of Patents and Trademarks*